Sept. 17, 1940. H. B. FABER ET AL Plant Pat. 421
CHERRY TREE
Filed April 18, 1940
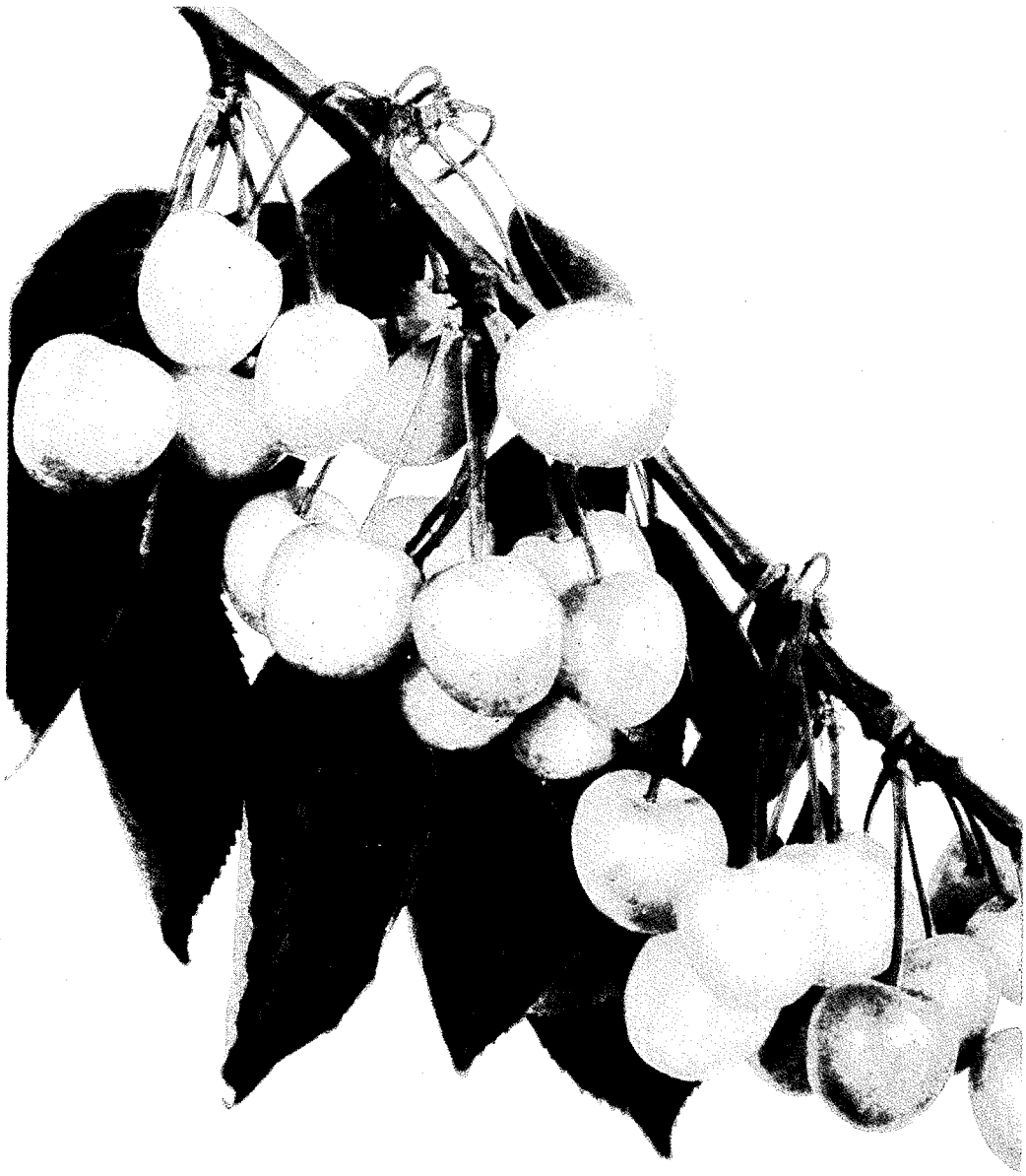
Inventors
H. B. Faber
J. A. E. Zigler Jr.
By Robb & Robb
Attorneys Patented Sept. 17, 1940

UNITED STATES PATENT OFFICE

421

CHERRY TREE

Horace B. Faber and John A. C. Ziegler, Jr., York, Pa., assignors to White Rose Seed & Nursery Co., York, Pa.

Application April 18, 1940, Serial No. 330,408

1 Claim. (Cl. 47—62)

The present invention relates to a new and distinct variety of Cherry Tree, the result of a definite effort to obtain a variety combining the desirable characteristics of two well known and established varieties "Napoleon" and "Schmidt's Bigarreau".

This new variety was originated by hybridizing the above named varieties, using Bigarreau as the pollen parent, and we find that said new variety resembles the Napoleon more nearly than any other sweet cherry, but that it definitely differs markedly from Napoleon in that it bears considerably more fruit and from either of the parents in respect to various other characteristics as will be set forth more particularly hereinafter.

While the new variety is a vigorous grower, of the spreading type, round-topped form, very hardy and prolific bearing as characteristic of the Napoleon, it is not as dense in its growth and the size of the fruit is much larger, a desired characteristic of Schmidt's Bigarreau.

Additionally, the fruit of Napoleon is much lighter than that of the new variety, the more intense or darker coloring of the latter coming apparently from the seed parent.

We find further a distinct difference in the foliage in that the leaves of the new variety are shorter and narrower than in the Napoleon.

In other minor respects, the new variety is novel and distinct, as will be noted in the following detail description in which the inherent or fixed color characteristics are specified in accordance with Ridgway's Color Standard:

Tree:

Large; vigorous; spreading; dense; round-topped; hardy; very productive; regular bearer.

Trunk:

Stocky; shaggy.

Branches:

Stocky; shaggy; brown with grayish bloom; dull.

Lenticels:

Numerous; medium size.

Leaves:

Large; length, 5¼ inches; width, $2\frac{7}{16}$ inches; ovate; lanceolate; acutely pointed; medium thick; rugose.

Color—Cress Green to Yew Green, Plate XXXI.

*Margin*—Glandular; coarsely serrate.

*Petiole*—Medium length; thick.

*Glands*—Average number, 2; Alternate; medium size; reniform; red; Position—at base of leaf blade.

Flower-Buds:

Hardy; medium size; long; conic; free; pubescent.

Flowers:

First and full bloom, April 10–15, York, Pa. Medium early compared with other varieties. Size—Medium; Color—White.

Fruit:

At maturity—eats hard.

*Size*—Large; Diameter Axial—$1\frac{5}{32}$ inches.

Transverse in suture plane—$1\frac{3}{16}$ inches.

At right angles to suture plane—1 inch.

*Form*—Variable; unsymmetrical; broadly conical.

*Base*—Rounded.

*Apex*—Depressed.

*Stem*—

Length—1½ to 1¾ inch.

Medium stout.

Adherence to stone—strong.

Color—Clear Fluorite Green, Plate XXXII, to Malachite Green, Plate XXXII.

*Skin*—

Medium thick; tough; astringent; tenacious to flesh.

Fruit colors unevenly, the fully colored cherries ranging from Nopal Red through Spectrum Red and Scarlet Red to Peach Red, with Salmon-Orange to Mikado Orange on the lighter cheeks, Plates I, II, III.

*Flesh*—

*Color*—Annam Buff, Plate XXIX.

*Amygdalin*—Juice—Moderate.

*Texture*—Firm; Fine; Meaty.

*Fibres*—Fine.

*Ripens*—Unevenly.

*Flavor*—Subacid.

*Aroma*—Wanting.

*Eating Quality*—Good.

*Stone*—Semifree.

*Size*—Medium.

Length—$\frac{5}{16}$ inch.

Breadth—¼ inch.

Thickness—$\frac{3}{16}$ inch.

*Form*—Obovoid.

*Base*—Straight; apex rounded.

*Sides*—Unequal; curved on right and left sides.

*Ridges*—Rounded.

*Pits*—Elongated; ventral edge, thick.

*Color of stone*—Honey Yellow, Plate XXV.
*Tendency to split*—No splitting.

Use:
Market; local; dessert; culinary; canning—all good.

Keeping Quality:
Good.

Resistance To:
Insects—Good.
Diseases—Good.

Shipping Quality:
Good.

What we claim is:

A new and distinct variety of Cherry Tree characterized as to novelty by its distinct habits of growth, size and shape of foliage, prolificacy of bearing, and large size and coloring of its fruit, substantially as shown and described.

HORACE B. FABER.
JOHN A. C. ZIEGLER, JR.